United States Patent [19]

Doumaux, Jr.

[11] Patent Number: 5,362,700

[45] Date of Patent: Nov. 8, 1994

[54] CATALYSTS AND PROCESS OF MAKING SAME FOR THE PRODUCTION OF LINEAR POLYAMINES

[75] Inventor: Arthur R. Doumaux, Jr., Charleston, W. Va.

[73] Assignee: Union Carbide Chemicals & Plastics Technology Corporation, Danbury, Conn.

[21] Appl. No.: 957,901

[22] Filed: Oct. 8, 1992

[51] Int. Cl.$^5$ .......................... B01J 37/08; B01J 27/18
[52] U.S. Cl. .................................................. 502/208
[58] Field of Search ............... 502/208, 209, 210, 211, 502/212, 213, 214

[56] References Cited

U.S. PATENT DOCUMENTS

| | | | |
|---|---|---|---|
| 2,824,073 | 2/1958 | Rylander et al. | 502/208 |
| 4,036,881 | 7/1977 | Brennan et al. | 260/583 P |
| 4,394,524 | 7/1983 | Ford et al. | 564/479 |
| 4,540,822 | 9/1985 | Vanderpool | 564/479 |
| 4,588,842 | 5/1986 | Vanderpool | 564/479 |
| 4,617,418 | 10/1986 | Ford et al. | 564/479 |
| 4,720,588 | 1/1988 | Turcotte et al. | 564/479 |
| 4,774,218 | 9/1988 | Shimasaki et al. | 502/208 X |
| 4,806,517 | 2/1989 | Vanderpool et al. | 502/208 |
| 4,827,037 | 5/1989 | Doumaux | 502/208 X |
| 4,910,342 | 3/1990 | Turcotte et al. | 564/479 |
| 4,973,569 | 11/1990 | Bowman et al. | 502/209 |
| 4,983,736 | 1/1991 | Doumaux et al. | 544/402 |
| 5,101,074 | 3/1992 | King et al. | 564/479 |
| 5,166,415 | 11/1992 | Doumaux et al. | 564/479 X |
| 5,202,489 | 4/1993 | Doumaux et al. | 564/479 |
| 5,202,492 | 4/1993 | Doumaux et al. | 564/479 X |
| 5,225,600 | 7/1993 | King et al. | 502/308 X |

FOREIGN PATENT DOCUMENTS

| | | |
|---|---|---|
| 0115138 | 8/1984 | European Pat. Off. |
| 0230776 | 8/1987 | European Pat. Off. |
| 0412613 | 2/1991 | European Pat. Off. |
| 0416674 | 3/1991 | European Pat. Off. |
| 0441685 | 8/1991 | European Pat. Off. |
| 0451898 | 10/1991 | European Pat. Off. |

*Primary Examiner*—Paul Lieberman
*Assistant Examiner*—Douglas McGinty
*Attorney, Agent, or Firm*—J. B. Mauro

[57] ABSTRACT

A catalyst composition for the condensation of alcohols with amines to produce an enhanced ratio of acyclic polyamines to other reaction products, comprising a reaction product of: (a) high surface area metal oxides or metal oxide precursors, or mixtures thereof, of metals selected from the group consisting of Groups 3, 4, 5, 6, 8, 12, 13, 14 and 15 of the Periodic Table, (b) a phosphorus component, and (c) metal oxides or metal oxide precursors, or mixtures thereof, of metals selected from the group consisting of Groups 1, 2, and 3 of the Periodic Table.

Also disclosed are methods for making the catalyst and for using it to manufacture predominantly linear polyamines.

7 Claims, 1 Drawing Sheet

CATALYSTS AND PROCESS OF MAKING SAME FOR THE PRODUCTION OF LINEAR POLYAMINES

BACKGROUND OF THE INVENTION

1. Field of the Invention

This invention relates to the catalytic condensation reaction of alcohols, e.g., monoethanolamine, with amines, e.g., ethyleneamine, to form predominantly acyclic polyethyleneamines at high levels of selectivity and conversion, and to the particular catalyst used.

2. Prior Art

The reaction of ethylene dichloride (EDC) with aqueous ammonia, followed by neutralization of the amine hydrochlorides formed with caustic, represents the predominant manufacturing process for making ethyleneamines for the last sixty years. Separation of the ethyleneamines products from the brine solution by extraction, dehydration, or evaporative crystallization, followed by separation and purification of the amines, can be an energy- and maintenance-intensive, corrosive process. Further, the co-production of salt requires an environmentally responsible method of disposal. This process produces the whole range of commercially acceptable ethyleneamines products, from ethylenediamine (EDA) to DETA, TETA, TEPA, PEHA, and the higher polyethylenepolyamines. Product distribution is controlled mainly by varying the ammonia:EDC mole ratio and/or the product recycle in the reactor feed.

A second commercially practiced process involves the reaction of ammonia and ethylene oxide to make monoethanolamine, followed by reductive amination to produce mainly the lower molecular weight ethyleneamines, EDA, DETA, etc. This process tends to produce a much higher level of unwanted cyclic ethyleneamines in comparison to the EDC-based process.

Monoethanolamine (MEA) can also be reacted with ethyleneamines such as EDA to produce the higher ethyleneamines. This newer process technology produces a highly acyclic product composition in comparison to the EDC-based process. Phosphorus-containing, acidic catalysts for the reaction of EDA and MEA are well known. Representative of the prior art are U.S. Pat. Nos. 4,806,517; 4,588,842; 4,540,822; 2,824,073; and the references cited in them. The art is also extensively discussed in co-pending, co-assigned U.S. patent application Ser. Nos. 390,706, filed Aug. 8, 1989, now U.S. Pat. No. 5,202,492; 390,829, filed Aug. 8, 1989, now U.S. Pat. No. 5,202,489; and 742,731, filed Aug. 6, 1991, now U.S. Pat. No. 5,225,660 the disclosures of which are incorporated herein by reference. The '517 and '842 patents represent versions of phosphorus-containing catalysts in which the phosphorus compound is "thermally chemically" bonded to a "thermally activated," pelletized group IVb metal oxide (e.g., titania) by treating preferably pre-formed pellets with the liquid phosphorus compound in solution form, and thereafter subjecting the pellets to a thermal process. The catalysts so produced are deficient, however, in that under typical commercial reaction conditions, the amines formed tend to leach critical catalytic elements, such as phosphorus, from the catalyst composition, or otherwise adversely affect the structural integrity of the pellets. As stated in U.S. Pat. No. 4,806,517, "in an extreme instance, catalyst pellets having good initial crush strength and surface hardness will be reduced to fines very rapidly," and/or will lose their activity or selectivity, under reaction conditions. Significant loss of structural integrity results in plugging downstream of the reactor and catalyst leaching may cause reforming in the later stages of product refining. The affected catalysts typically tend to age rapidly.

Co-assigned U.S. Pat. No. 4,983,736, the disclosure of which is incorporated herein by reference, describes catalysts related to those of the present invention; however, the patented catalysts are disclosed as calcined at significantly lower temperatures.

SUMMARY OF THE INVENTION

Figure 1:
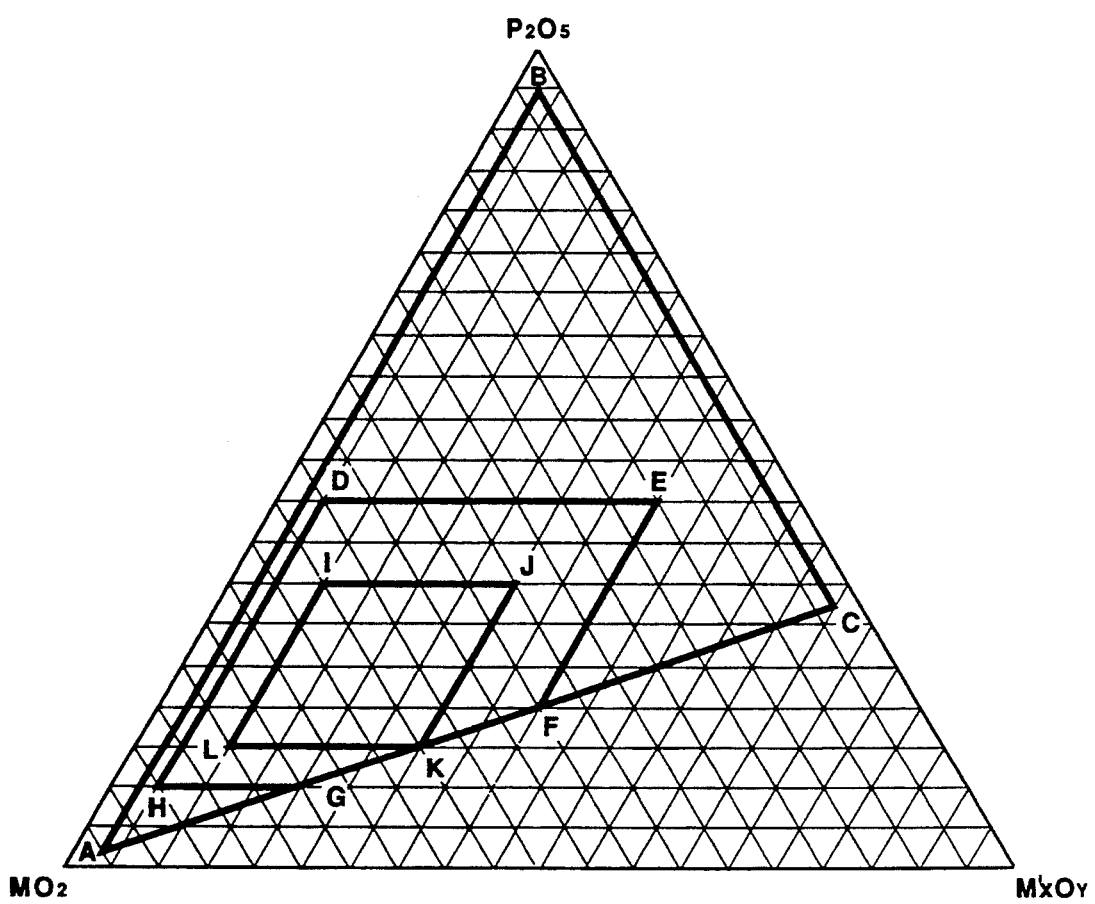
FIG. 1 is a ternary diagram depicting preferred catalyst compositions of the invention in mole percent of the active components.

The present invention provides a catalyst composition for the condensation of alcohols with amines to produce an enhanced ratio of acyclic polyamines to other reaction products, wherein the catalyst composition is formed by chemically reacting three different reaction components comprising: (a) high surface area metal oxides or metal oxide precursors of metals selected from the group consisting of Groups 3, 4, 5, 6, 8, 12, 13, 14 and 15 of the Periodic Table, (b) one or more phosphorus compounds, and (c) metal oxides or metal oxide precursors of metals selected from the group consisting of Groups 1, 2, and 3 of the Periodic Table. Alternatively, if desired for the sake of manufacturing convenience or otherwise, component (a) may be combined with a preformed, reactive material prepared by reacting the (b) and (c) components.

Preferably, the catalyst composition comprises about 10 to about 50, preferably about 15 to about 40, mole percent phosphorus compound calculated as $P_2O_5$, about 5 to about 40, preferably about 20 to about 30, mole percent, calculated as an oxide or oxides (if a mixture of compounds is used), of a Group 1, 2 or 3 metal or metals, and the remainder being an oxide of a Group 4, 5, 6, 8, 12, 13, 14 or 15 metal or metals.

More particularly, where component (a) comprises titania or zirconia, the present invention provides a catalyst composition wherein the composition of the principal catalytic components, exclusive of other materials which may be in the fully formulated composition, falls within the compositional area defined by points A-B-C-A of the ternary diagram which is FIG. 1. Preferably, the catalyst composition falls within the compositional area defined by points D-E-F-K-G-H-D of FIG. 1. More preferably, the catalyst composition falls within the compositional area defined by points I-J-K-L-I of FIG. 1.

In addition, the present invention comprises a method for making a catalyst composition for the condensation of alcohols with amines to produce an enhanced ratio of acyclic polyamines to other reaction products, comprising chemically reacting at a temperature of at least about 350° C. components (a), (b) and (c), above, for a period of time sufficient to produce at least one catalytically active phosphate species. Of the metals of component Na is preferred. Of the metals of component (a), Ti and Zr are preferred.

The invention further comprises a process for the production of predominantly acyclic polyamines, comprising the condensation of one or more alcohols with one or more amines at a temperature of about 125° to about 400° C., a pressure of about 50 to about 3000 psig, and a space velocity of about 1 to about 50 gram-moles/hour/kilogram of catalyst, in the presence of a catalyst of claim

DETAILED DESCRIPTION

The catalysts described in U.S. Pat. No. 4,983,736, prepared from high surface area metal oxides such as anatase titania and various phosphate precursors, while quite active and selective, were calcined at relatively low temperatures. It may, however, be desirable to calcine at temperatures significantly above 400° C., where commercial crush strengths can be obtained. However, high calcination temperatures are often associated with loss of activity. The catalysts of U.S. Pat. No. 4,983,736 exhibit free and bound phosphate species attributable to the phosphate precursor used. In the catalysts of the instant invention, which are subjected to higher calcination temperatures, species not observed in the prior art catalysts result from the combination of the claimed components into new phosphate species. Thus, a key improvement over the catalysts described in U.S. Pat. No. 4,983,736 by the newer catalysts of this invention is that, in the earlier catalysts, reaction between the phosphate precursor and the metal oxide involved mainly the surface hydroxyl groups to produce the active species, whereas in the catalysts of this invention, the bulk metal oxide reacts with the phosphate precursors to form the new phosphate species. These new species are thought to comprise the improved catalyst system of this invention. In fact, at temperatures greater than about 350° C., the metal oxide and phosphate precursors begin to react to produce a number of different phosphate species.

In general, higher levels of phosphate precursor are required to prepare the better catalysts. Not wanting to be bound by any theory, these reaction products represent a neutralization reaction with metal oxide acting as a base, and the phosphate, in relative sense, acting as an acid. The final catalysts, when titania is used, exhibit pH values, as aqueous slurries, from about 3 to about 11. The more preferred catalysts, described later, have pH values about 9, and their basicity may explain their inherent stability. High surface area, mildly acidic or amphoteric hydrous metal oxides or mixtures of these seem to be required for reaction with the other components to produce final catalyst compositions which are active, selective, and stable under actual reaction conditions for making alkyleneamines.

As indicated, one of the required components is a metal oxide, or mixtures thereof, or their precursors (such as metal alkoxides, metal hydroxides, metal halides, or the like or mixtures thereof) selected from the group consisting of the metals of Groups 3, 4, 5, 6, 8, 12, 13, 14 and 15 metals, and mixtures thereof. The preferred metal oxides are amphoteric or slightly acidic or slightly basic, are hydrous, and have high surface areas. While various such materials are well known in the catalyst art as inert supports, it is noteworthy that such materials as claimed herein are demonstratively reactive in forming the present catalyst compositions, as opposed to serving the usual prior art function of merely supporting the active materials. These reactive metal oxides can be used singly, as mixtures, or in combination with others. Illustrative of metal oxides which may be used include, for example, $TiO_2$, $ZrO_2$, $La_2O_3$, $Fe_2O_3$, $ZnO$, $Nb_2O_5$, $WO_3$, $Ta_2O_5$, $TiO_2$—$SiO_2$, $TiO_2$—$CdO$, $TiO_2$—$Bi_2O_3$, $TiO_2$—$Sb_2O_5$, $TiO_2$—$SnO_2$, $TiO_2$—$ZrO_2$, $TiO_2$—$BeO$, $TiO_2$—$MgO$, $TiO_2$—$CaO$, $TiO_2$—$SrO$, $TiO_2$—$ZnO$, $TiO_2$—$Ga_2O_3$, $TiO_2$—$Y_2O_3$, $TiO_2$—$La_2O_3$, $TiO_2$—$Fe_2O_3$, $TiO_2$—$WO_3$, $TiO_2$—$V_2O_5$, $TiO_2$—$Na_2O$, $TiO_2$—$BaO$, $TiO_2$—$CaO$, $TiO_2$—$HfO_2$, $TiO_2$—$Li_2O$, $TiO_2$—$Nb_2O_5$, $TiO_2$—$Ta_2O_5$, $TiO_2$—$Gd_2O_3$, $TiO_2$—$Lu_2O_3$, $TiO_2$—$Yb_2O_3$, $TiO_2$—$CeO_2$, $TiO_2$—$Sc_2O_3$, $TiO_2$—$PbO$, $TiO_2$—$B_2O_3$, $ZrO_2$—$SiO_2$, $ZrO_2$—$Al_2O_3$, $ZrO_2$—$SnO$, $ZrO_2$—$Nb_2O_5$, $ZrO_2$—$Ta_2O_5$, $ZrO_2$—$MoO_3$, $ZrO_2$—$WO_3$, $ZrO_2$—$TiO_2$, $ZrO_2$—$HfO_2$, $TiO_2$—$SiO_2$—$Al_2O_3$, $TiO_2$—$SiO_2$—$ZnO$, $TiO_2$—$SiO_2$—$ZrO_2$, $TiO_2$—$SiO_2$—$MgO$, $TiO_2$—$SiO_2$—$Fe_2O_3$, $TiO_2$—$SiO_2$—$B_2O_3$, $TiO_2$—$SiO_2$—$WO_3$, $TiO_2$—$SiO_2$—$Na_2O$, $TiO_2$—$SiO_2$—$MgO$, $TiO_2$—$SiO_2$—$La_2O_3$, $TiO_2$—$SiO_2$—$Nb_2O_5$, $TiO_2$—$SiO_2$—$Bi_2O_3$, $TiO_2$—$Al_2O_3$—$ZnO$, $TiO_2$—$Al_2O_3$—$ZrO_2$, $TiO_2$—$Al_2O_3$—$Fe_2O_3$, $TiO_2$—$Al_2O_3$—$WO_3$, $TiO_2$—$Al_2O_3$—$La_2O_3$, $ZrO_2$—$SiO_2$—$Al_2O_3$, $ZrO_2$—$SiO_2$—$SnO$, $ZrO_2$—$SiO_2$—$Nb_2O_5$, $ZrO_2$—$SiO_2$—$WO_3$, $ZrO_2$—$SiO_2$—$TiO_2$, $ZrO_2$—$SiO_2$—$HfO_2$, $ZrO_2$—$SiO_2$—$Ta_2O_5$, $ZrO_2$—$Al_2O_3$—$SiO_2$, $ZrO_2$—$Al_2O_3$—$PbO$, $ZrO_2$—$Al_2O_3$—$Nb_2O_5$, $ZrO_2$—$Al_2O_3$—$WO_3$, $ZrO_2$—$Al_2O_3$—$TiO_2$, $ZrO_2$—$HfO_2$—$Al_2O_3$, $ZrO_2$—$HfO_2$—$TiO_2$, and the like. Other suitable mixed metal oxide catalysts embraced within the scope of this invention are disclosed by Tanabe et al., Bulletin of the Chemical Society of Japan, Vol. 47(5), pp. 1064–1066 (1974). High surface area titania and zirconia, or mixed metal oxides of high surface area titania and zirconia, are the preferred metal oxides of this invention.

Another required component is phosphorusbearing. The source of the phosphorus is not narrowly critical. Phosphoric acid, phosphorus acid, polyphosphoric acid, pyrophosphoric acid, their ammonium, or amine salts, esters, or anhydrides serve as typical but not limiting examples.

The third necessary component is a Group 1, 2, or 3 metal oxide or mixtures thereof, or their precursors, such as acetate, carbonate, oxalate, nitrate salts or mixtures thereof, which serve as typical but not limiting examples, in combination with, and/or optionally prereacted with, the phosphorus component noted above. Typical but not limiting, examples of Groups 1, 2 and 3 metals combinations with phosphorus components include orthophosphate salts, such as $NaH_2PO_4$, $LiH_2PO_4$, $KH_2PO_4$, $Na_2HPO_4$, $Ba(H_2PO_4)_2$, $Mg(H_2PO_4)_2$, $Ca(H_2PO_4)_2$, $La(H_2PO_4)_2$, $Ln(H_2PO_4)_2$; dihydrogenpyrophosphate salts such as $Na_2H_2P_2O_7$, $Li_2H_2P_2O_7$, $CaH_2P_2O_7$, $MgH_2P_2O_7$, $BaH_2P_2O_7$, $SrH_2P_2O_7$; tripolyphosphate salts such as $Na_3H_2P_3O_{10}$, or cyclic metaphosphates such as $Na_3P_3O_9$, $LiP_3O_9$, $Na_4P_4O_{12}$. Especially preferred second and third component combinations include $NaH_2PO_4$, $LiH_2PO_4$, $Na_2H_2P_2O_7$, $Na_3H_2P_3O_{10}$, $Na_3P_3O_9$, $LiNa_2P_3O_9$, $KNa_2P_3O_9$, $NaBaP_3O_9$, $NaLaP_4O_{12}$, $Na_2CaP_4O_{12}$, $Mg_2P_4O_{12}$, $KCaP_3O_9$, and mixtures of these.

The catalysts of this invention may be prepared by intimately mixing a damp hydrous, high surface area metal oxide of the Group 3, 4, 5, 6, 8, 12, 13, 14, or 15 metal with a phosphorus component and a metal oxide component of Group 1, 2, or 3, or a preformed component comprising the phosphorus-Group 1, 2, or 3 components, to produce a dough which is then extruded, pelletized, dried and calcined, utilizing techniques known in the art. As opposed to the typical catalysts of the prior art, which are made by washing a pre-formed support with an aqueous solution of the phosphate compound, the catalysts of this invention are unsupported, insoluble materials which are prepared in bulk in the solid phrase as described above, and are not applied to a separate carrier or support.

It is characteristic of the catalysts of this invention that a period of thermal treatment is desirable. Such treatment can occur either during calcination or under reaction conditions, or some combination thereof. Under these conditions the components are transformed into the active bulk catalyst. Suitable catalyst species appear to be formed as a result of calcination at about 350° to about 850° C., preferably about 400° to about 700° C. and most preferably about 425° to about 625° C., for a period of at least about 0.5 hour, preferably for a period of about 2 to about 3 hours. The time period may depend on equipment used, as known to those skilled in the ark.

Especially preferred catalyst compositions, expressed in mole percent, are portrayed in the tenary diagram shown in FIG. 1. The preferred first component, the metal oxide, $MO_2$, is represented by $TiO_2$, $ZrO_2$, and mixtures thereof. The preferred third component, the metal oxide $M'_xO_y$, wherein x is 1 or 2 and y is 1 or 3, is represented by $Na_2O$, $Li_2O$, $BaO$, $K_2O$, and $La_2O_3$, and mixtures thereof. These catalyst compositions are effective in condensing alcohols with amines to produce an enhanced ratio of acyclic polyamines, wherein the catalyst composition falls within the compositional area defined by points A-B-C-A of FIG. 1. Preferably, the catalyst composition falls within the compositional area defined by the points D-E-F-K-G-H-D of FIG. 1. More preferably, the catalyst composition falls within the compositional area defined by points I-J-K-L-I of FIG. 1.

When more than three metals are used, the position of the resulting composition on the ternary diagram is obtained by employing the following formula: [Σ Mole % of each $MO_2$+[Mole % $P_2O_5$+[Σ Mole % of each $MO_2$]=100.

The catalyst compositions are preferably subjected to a temperature of at least about 350° C. for a period of time sufficient to produce at least one catalytically active phosphate species.

In FIG. 1, the lettered points represent the following compositions:

|   | $MO_2$ | $P_2O_5$ | $M'_xO_y$ |
|---|---|---|---|
| A | 95 | 2.5 | 2.5 |
| B | 2.5 | 95 | 2.5 |
| C | 2.5 | 33 | 64.5 |
| D | 50 | 45 | 5 |
| E | 15 | 45 | 40 |
| F | 40 | 20 | 40 |
| G | 70 | 10 | 20 |
| H | 85 | 10 | 5 |
| I | 55 | 35 | 10 |
| J | 35 | 35 | 30 |
| K | 55 | 15 | 30 |
| L | 75 | 15 | 10 |

The preferred catalysts, as opposed to the acidic catalysts of the prior art, are neutral or are mildly to moderately basic, as determined by the pH of an aqueous slurry of the catalyst composition i.e., have a pH greater than about 7. In general, pH increases with calcining temperature; however, calcination at over about 850° C. can produce a decrease in pH and lead to stable catalyst compositions, but having reduced activity.

As opposed to the typical catalysts of the prior art, which are made by washing a pre-formed support with an aqueous solution of the phosphate compound, the catalysts of this invention are solid, insoluble materials which are prepared in bulk in the solid phase, as described above. Thus, pellets or other shapes made from the instant compositions appear to be catalytically active throughout, instead of merely on their surface, and specific geometry of the catalyst pellets or other shapes is not considered to be critical.

It has been observed that treatment of the catalysts of this invention with water or steam may, in some instances, reduce the thermal treatment period which would otherwise be required. For example, calcining in the presence of steam at temperatures of about 400° C. or more, or passing steam over calcined catalyst at about 250° C. or more and about 500 psig or more for about 5 to about 48 hours, preferably about 300° C. and about 600 psig for about 24 hours, can significantly reduce the thermal treatment period of some catalyst compositions.

The reaction of the alcohol and the amine, using the catalysts of this invention, may be effected under conditions known in the art. A broad range of amine:alcohol mole ratios may be successfully employed, e.g., about 0.5:1 to about 6:1, preferably about 1:1 to about 4:1. While the reaction temperature may be in the range of about 125° to about 400° C., it is preferred that a range of about 225° to about 325° C. be used. Pressures may range from about 50 to about 3000 psig, but a range of about 200 to about 2000 psig is preferred. Space velocities of about 1 to about 50, preferably about 3 to about 25, and most preferably about 5 to about 15, gram-moles/hour/kilogram of catalyst may be used. It will be appreciated by those skilled in the art that the reaction conditions indicated are merely those recommended, and are not intended to be construed as limitations on the catalysts or processes of the invention.

It is to be appreciated that the catalysts of this invention may also be useful in the production of alkylamines. For example, an alcohol and at least one of a primary amine, a secondary amine or a tertiary amine may be contacted in the presence of a catalyst of this invention under conditions effective to produce alkylamines.

The reactants used in the condensation process of the invention may be ammonia or one or more organic compounds containing —NH— and any reactive compound possessing an alcoholic hydroxyl group, subject to the following: the intramolecular condensation of an amino compound produces an amine having a lower molecular weight, and the intermolecular condensation of an amino compound with one or more of another amino compound or a compound containing an alcoholic hydroxyl group produces an amine having a lower, same or higher molecular weight than the reactants.

Illustrative of suitable reactants in effecting the process of the invention, include by way of example:

|   | Ammonia |
|---|---|
| MEA | monoethanolamine |
| EDA | ethylenediamine |
| MeEDA | methylethylenediamine |
| EtEDA | ethylethylenediamine |
| AEEA | N-(2-aminoethyl)ethanolamine |
| HEP | N-(2-hydroxyethyl)piperazine |
| DETA | diethylenetriamine |
| AEP | N-(2-aminoethyl)piperazine |

-continued

| | |
|---|---|
| TETA | triethylenetetramine |
| TEPA | tetraethylenepentamine |
| PEHA | pentaethylenehexamine |
| | TETA Isomers: |
| TAEA | trisaminoethylamine |
| TETA | triethylenetetramine |
| DPE | dipiperazinoethane |
| DAEP | diaminoethylpiperazine |
| PEEDA | piperazinoethylethylenediamine |
| | TEPA Isomers: |
| AETAEA | aminoethyltrisaminoethylamine |
| TEPA | tetraethylenepentamine |
| AEDPE | aminoethyldipiperazinoethane |
| AEPEEDA | aminoethylpiperazinoethyl-ethylenediamine |
| iAEPEEDA | isoaminoethylpiperazinoethyl-ethylenediamine |
| AEDAEP | aminoethyldiaminoethylpiperazine |
| BPEA | bispiperazinoethylamine |

The foregoing also can represent the products of the reaction. For example, ammonia and MEA are frequently employed to produce EDA along with a variety of other amines, most of which are set forth above.

Glycol compounds can also be employed in the preparation of amines in accordance with this invention. For purposes of this invention, glycol compounds embrace diols and polyols. Illustrative of suitable glycol compounds include alkylene glycols such as ethylene glycol, propylene glycol, 1,3-propane diol, or mixtures thereof.

The process may be effected in the liquid or vapor or supercritical liquid states or mixtures thereof. In this context, the vapor phase reaction is intended to refer to the general vapor state of the reactants, including a pressure range of about 50 to about 3,000 psi.

The reaction may be effected by the incremental addition of any of the reactants to any others, or by the joint addition of the reactants to the catalyst. The preferred process effects the reaction in a continuous manner over a fixed bed of the catalyst in a tubular reactor. However, the reaction may be carried out by slurrying the catalyst in the reactants or in a batch mode in an autoclave. An inert such as nitrogen, methane, and the like, can be used in the reaction process, as is known in the art.

The preferred process involves the formation of alkyleneamines from the intermolecular condensation of alkanolamines and alkyleneamines or the intramolecular condensation of alkyleneamines or alkanolamines. Illustrative of such reactions are the following reactant combinations:

| REACTANT | REACTANT | PRODUCTS |
|---|---|---|
| Ammonia | Methanol | Monomethylamine Dimethylamine Trimethylamine |
| Ammonia | MEA | EDA, DETA, AEEA, TETA, TEPA, PIP |
| Ammonia | AEEA | DETA, PIP |
| MEA, Ammonia | EDA | EDA, AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| MEA | EDA | AEEA, HEP, DETA, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA |
| EDA | AEEA | HEP, AEP, TETA, TEPA, PEHA, TETA Isomers: TAEA, TETA, DAEP, PEEDA, DPE TEPA, TEPA Isomers: AETAEA, AEPEEDA, AEDAEP, AEDPE, BPEA DETA AEEA TEPA Isomers, AEP |
| EDA | EDA | DETA, TETA AND TEPA Isomers |

The process of the invention provides the ability to generate the desirable higher polyalkylene polyamine products such as TETA, TEPA and PEHA without generating large amounts of cyclic alkylenepolyamine products such as PIP, AEP and HEP.

In the examples set forth in the tables below, the catalyst of choice was placed in one or more of three tubular reactors, each having an outside diameter of 1 inch and an overall length of 24 inches. A small amount of glass beads and glass wool was placed at the top and bottom of the catalyst bed to keep the catalyst from shifting. The catalyst portion of the reactor was sufficient for accommodating 100 cubic centimeters of catalyst. The reactor tubes were made of 316 stainless steel. Heat was provided by immersing the reactor tubes in a heated sand bath.

The catalysts employed in the examples below were prepared by admixing the indicated gram weight of high surface area titania (taking into account the loss on ignition, i.e., the water loss), phosphate compounds and other compounds in a amounts indicated, and a quantity of water, adjusted to provide an extrudable dough. The catalyst compositions were extruded and the extrudate was randomly pelletized. Compositions of the green catalysts are shown in Table I. The extrudate was dried and calcined as indicated, the resulting catalysts having the physical characteristics indicated in Table II.

TABLE I

| CATALYST COMPOSITIONS, WEIGHT % | | | | | | | | | |
|---|---|---|---|---|---|---|---|---|---|
| | A | B | C | D | E | F | G | H | I |
| $TiO_2$ | 48.81 | 29.36 | 35.80 | 48.81 | 25.81 | 37.17 | 53.79 | 58.87 | 53.79 |
| $Al_2O_3$ | | | | | | | | | |
| $Na_3[P_3O_9]$ | 45.30 | 42.82 | 8.31 | 45.30 | 47.05 | 52.70 | 34.32 | 23.11 | 34.32 |
| $H_3PO_4$ | | | 55.89 | | 27.14 | 10.13 | | | |
| $Na_2CO_3$ | 5.89 | 27.82 | | 5.89 | | | 11.89 | 18.02 | 11.89 |
| $NaH_2PO_4$ | | | | | | | | | |
| $NaBa(P_3O_9)$ | | | | | | | | | |
| $NaLa(P_4O_{12})$ | | | | | | | | | |

TABLE I-continued

CATALYST COMPOSITIONS, WEIGHT %

| | | | | | | | | | |
|---|---|---|---|---|---|---|---|---|---|
| $K_2CO_3$ | | | | | | | | | |
| $Li_2CO_3$ | | | | | | | | | |
| $KPO_3$ | | | | | | | | | |
| Drying Temp., °C. | 165 | 165 | 165 | 165 | 165 | 165 | 165 | 165 | 165 |
| Calc. Temp., °C. | 450 | 450 | 600 | 600 | 600 | 525 | 450 | 450 | 600 |

| | J | K | L | M | N | O | P | Q | R |
|---|---|---|---|---|---|---|---|---|---|
| $TiO_2$ | 43.08 | 43.93 | 39.94 | 39.94 | 40.08 | 37.63 | 48.02 | 46.72 | 49.25 |
| $Al_2O_3$ | | | 9.09 | 9.09 | | | | | |
| $Na_3[P_3O_9]$ | 43.98 | 56.07 | 50.97 | 50.97 | | | 44.57 | 36.13 | 45.71 |
| $H_3PO_4$ | | | | | | | | | |
| $Na_2CO_3$ | | | | | | | 2.90 | | 2.97 |
| $NaH_2PO_4$ | 12.94 | | | | | | | | |
| $NaBa(P_3O_9)$ | | | | | | 62.37 | | | |
| $NaLa(P_4O_{12})$ | | | | | 59.92 | | | | |
| $K_2CO_3$ | | | | | | | 4.51 | 8.78 | |
| $Li_2CO_3$ | | | | | | | | | 2.07 |
| $KPO_3$ | | | | | | | | 8.37 | |
| Drying Temp., °C. | 165 | 110 | 165 | 165 | 165 | 165 | 165 | 165 | 165 |
| Calc. Temp., °C. | 450 | 600 | 350 | 600 | 600 | 600 | 450 | 450 | 450 |

TABLE II

CATALYST COMPOSITION AND CHARACTERISTICS

| Catalyst Identifier | FIG. 1 Catalyst Composition Mole % | | Physical Characteristics |
|---|---|---|---|
| A | 20% | $P_2O_5$ | Size: 1/16-in extrudates |
| | 55% | $TiO_2$ | Surface area: 12.7 m2/gr |
| | 25% | $Na_2O$ | Pore Vol.: 0.152 cc/gr |
| | | | Pore Size: 920A |
| | | | Crush Strength: 1.4 lbs. |
| B | 20% | $P_2O_5$ | Size: 1/16-in extrudates |
| | 35% | $TiO_2$ | Surface area: 16.5 m2/gr |
| | 45% | $Na_2O$ | Pore Vol.: 0.203 cc/gr |
| | | | Pore Size: 920A |
| | | | Crush Strength: 1.1 lbs. |
| C | 40% | $P_2O_5$ | Size: 1/16-in extrudates |
| | 55% | $TiO_2$ | Surface area: 0.9 m2/gr |
| | 5% | $Na_2O$ | Pore Vol.: 0.152 cc/gr |
| | | | Pore Size: 7400A |
| | | | Crush Strength: 0 lbs. |
| D | 20% | $P_2O_5$ | Size: 1/16-in extrudates |
| | 55% | $TiO_2$ | Surface area: 4.4 m2/gr |
| | 25% | $Na_2O$ | Pore Vol.: 0.140 cc/gr |
| | | | Pore Size: 900A |
| | | | Crush Strength: 12.1 lbs. |
| E | 40% | $P_2O_5$ | Size: 1/16-in extrudates |
| | 35% | $TiO_2$ | Surface area: 2.0 m2/gr |
| | 25% | $Na_2O$ | Pore Vol.: 0.162 cc/gr |
| | | | Pore Size: 10600A |
| | | | Crush Strength: 4.8 lbs. |
| F | 30% | $P_2O_5$ | Size: 1/16-in extrudates |
| | 45% | $TiO_2$ | Surface area: 2.1 m2/gr |
| | 25% | $Na_2O$ | Pore Vol.: 0.064 cc/gr |
| | | | Pore Size: 1630A |
| | | | Crush Strength: 8.5 lbs. |
| G | 15% | $P_2O_5$ | Size: 1/16-in extrudates |
| | 60% | $TiO_2$ | Surface area: 26.1 m2/gr |
| | 25% | $Na_2O$ | Pore Vol.: 0.105 cc/gr |
| | | | Pore Size: 162A |
| | | | Crush Strength: 10.6 lbs. |
| H | 10% | $P_2O_5$ | Size: 1/16-in extrudates |
| | 65% | $TiO_2$ | Surface area: 26.2 m2/gr |
| | 25% | $Na_2O$ | Pore Vol.: 0.101 cc/gr |
| | | | Pore Size: 107A |
| | | | Crush Strength: 11.6 lbs. |
| I | 15% | $P_2O_5$ | Size: 1/16-in extrudates |
| | 60% | $TiO_2$ | Surface area: 8.9 m2/gr |
| | 25% | $Na_2O$ | Pore Vol.: 0.135 cc/gr |
| | | | Pore Size: 351A |
| | | | Crush Strength: 22.4 lbs. |
| J | 25% | $P_2O_5$ | Size: 1/16-in extrudates |
| | 50% | $TiO_2$ | Surface area: 4.64 m2/gr |
| | 25% | $Na_2O$ | Pore Vol.: 0.147 cc/gr |
| | | | Pore Size: 1210A |
| | | | Crush Strength: 15.1 lbs. |
| K | 25% | $P_2O_5$ | Size: 1/16-in extrudates |
| | 50% | $TiO_2$ | Surface area: 2.92 m2/gr |
| | 25% | $Na_2O$ | Pore Vol.: 0.184 cc/gr |
| | | | Pore Size: 1600A |
| | | | Crush Strength: 22.7 lbs. |
| L | 23.0% | $P_2O_5$ | Size: 1/16-in extrudates |
| | 45.9% | $TiO_2$ | Surface area: 37.5 m2/gr |
| | 23.0% | $Na_2O$ | Pore Vol.: 0.185 cc/gr |
| | 8.2% | $Al_2O_3$ | Pore Size: 430A |
| | | | Crush Strength: 3.4 lbs. |
| M | 23.0% | $P_2O_5$ | Size: 1/16-in extrudates |
| | 45.9% | $TiO_2$ | Surface area: 13.1 m2/gr |
| | 23.0% | $Na_2O$ | Pore Vol.: 0.172 cc/gr |
| | 8.2% | $Al_2O_3$ | Pore Size: 2450A |
| | | | Crush Strength: 19.6 lbs. |
| N | 28.6% | $P_2O_5$ | Size: 1/16-in extrudates |
| | 57.1% | $TiO_2$ | Surface area: 26.5 m2/gr |
| | 7.1% | $Na_2O$ | Pore Vol.: 0.120 cc/gr |
| | 7.1% | $La_2O_3$ | Pore Size: 220A |
| | | | Crush Strength: 2.1 lbs. |
| O | 25% | $P_2O_5$ | Size: 1/16-in extrudates |
| | 50% | $TiO_2$ | Surface area: 3.4 m2/gr |
| | 8.3% | $Na_2O$ | Pore Vol.: 0.181 cc/gr |
| | 16.7% | BaO | Pore Size: 1250 A |
| | | | Crush Strength: 15.2 lbs. |
| P | 20% | $P_2O_5$ | Size: 1/16-in extrudates |
| | 55% | $TiO_2$ | Surface area: 4.3 m2/gr |
| | 22.5% | $Na_2O$ | Pore Vol.: 0.225 cc/gr |
| | 2.5% | $K_2O$ | Pore Size: 1303 A |
| | | | Crush Strength: 28.1 lbs. |
| Q | 20% | $P_2O_5$ | Size: 1/16-in extrudates |
| | 55% | $TiO_2$ | Surface area: 1.7 m2/gr |
| | 16.7% | $Na_2O$ | Pore Vol.: 0.231 cc/gr |
| | 8.3% | $K_2O$ | Pore Size: 1557 A |
| | | | Crush Strength: 43.3 lbs. |
| R | 20% | $P_2O_5$ | Size: 1/16-in extrudates |
| | 55% | $TiO_2$ | Surface area: 8.5 m2/gr |
| | 22.5% | $Na_2O$ | Pore Vol.: 0.138 cc/gr |
| | 2.5% | $Li_2O$ | Pore Size: 258 A |
| | | | Crush Strength: 30.2 lbs. |

EXAMPLES

In the examples below, the following legend applies to various of the abbreviations used:

| ID | identification |
|---|---|
| T | Temperature, °C. |
| P | Pressure, psig |
| too | time on organics |
| SVM | space velocity, gram-mole alcohol feed (monoethanolamine)/Kg catalyst/hour |
| EtoM | Ethylenediamine to monoethanolamine feed mole ratio |
| XM | % conversion monoethanolamine |
| XE | % conversion ethylenediamine |
| DtoA | diethylenetriamine to aminoethylethanolamine weight ratio |
| DtoP | diethylenetriamine to piperazine weight ratio |
| N4nc | ratio of 100 × (L-TETA + TAEA)/total TETAs |

| | | Example | | | | | | | | | |
|---|---|---|---|---|---|---|---|---|---|---|---|
| | | 1 | 2 | 3 | 4 | 5 | 6 | 7 | 8 | 9 | 10 |
| Catalyst | ID | A | A | A | A | A | A | A | A | A | A |
| Operating Conditions | T | 300 | 300 | 310 | 290 | 290 | 300 | 290 | 290 | 300 | 290 |
| | P | 614.7 | 614.7 | 614.7 | 614.7 | 614.7 | 614.7 | 614.7 | 614.7 | 614.7 | 614.7 |
| | too | 24 | 118.6 | 213.2 | 309 | 412.2 | 514 | 610.6 | 706.7 | 802.7 | 1011.7 |
| | SVM | 11.26 | 12.14 | 13.41 | 12.48 | 11.95 | 10.06 | 16.48 | 12.99 | 11.91 | 12.64 |
| | EtoM | 1.99 | 1.99 | 1.99 | 1.99 | 1.99 | 1.99 | 1.99 | 1.99 | 1.99 | 1.99 |
| Calculated Results | XM | 22.59 | 33.62 | 47.31 | 22.93 | 25.70 | 38.73 | 19.85 | 19.89 | 33.73 | 22.55 |
| | XE | 9.49 | 13.35 | 14.54 | 10.59 | 8.85 | 14.92 | 9.22 | 9.85 | 12.57 | 9.86 |
| | DtoA | 7.28 | 6.28 | 9.52 | 4.64 | 5.04 | 5.74 | 3.98 | 4.10 | 5.06 | 3.97 |
| | DtoP | 19.84 | 25.34 | 19.85 | 25.44 | 25.37 | 25.68 | 28.77 | 26.06 | 25.30 | 27.65 |
| | N4nc | 100.00 | 100.00 | 100.00 | 100.00 | 100.00 | 100.00 | 100.00 | 100.00 | 100.00 | 100.00 |
| Product Composition | PIP | 3.16 | 2.53 | 2.99 | 2.58 | 2.74 | 2.56 | 2.39 | 2.62 | 2.64 | 2.45 |
| | DETA | 62.71 | 64.02 | 59.27 | 65.63 | 69.44 | 65.76 | 68.75 | 68.31 | 66.70 | 67.87 |
| (reactant and | AEEA | 8.62 | 10.20 | 6.22 | 14.14 | 13.78 | 11.46 | 17.29 | 16.67 | 13.19 | 17.11 |
| water-free basis) | AEP | 1.11 | 1.32 | 1.97 | 1.04 | 1.16 | 1.40 | .98 | 1.05 | 1.26 | 1.01 |
| | N4 | 5.41 | 8.66 | 10.59 | 6.37 | 5.10 | 7.85 | 5.05 | 3.74 | 7.26 | 3.47 |
| | N5 | 0.00 | 0.00 | 0.00 | 0.00 | 0.00 | 0.00 | 0.00 | 0.00 | 0.00 | 0.00 |
| | other | 17.68 | 12.11 | 17.97 | 9.30 | 6.93 | 10.15 | 4.84 | 6.94 | 8.20 | 7.39 |
| Leaching | P, ppm | 3.38 | 1.4 | 1.57 | 1.08 | <1 | <1 | <1 | <1 | <1 | <1 |

| | | Example | | | | | | | | | |
|---|---|---|---|---|---|---|---|---|---|---|---|
| | | 11 | 12 | 13 | 14 | 15 | 16 | 17 | 18 | 19 | 20 |
| Catalyst | ID | B | B | B | B | C | C | C | D | D | D |
| Operating Conditions | T | 300 | 310 | 310 | 300 | 300 | 300 | 300 | 300 | 300 | 310 |
| | P | 614.7 | 614.7 | 614.7 | 614.7 | 614.7 | 614.7 | 614.7 | 614.7 | 614.7 | 614.7 |
| | too | 6 | 97 | 192.5 | 217 | 72 | 178.1 | 274.3 | 24 | 118.6 | 213.2 |
| | SVM | 19.41 | 16.53 | 17.41 | 17.28 | 8.64 | 19.01 | 17.50 | 59.00 | 11.07 | 11.96 |
| | EtoM | 1.99 | 1.99 | 1.99 | 1.99 | 1.99 | 1.99 | 1.99 | 1.99 | 1.99 | 1.99 |
| Calculated Results | XM | 0.5 | 1.0 | 0.8 | 2.9 | 86.28 | 9.25 | 9.26 | 15.47 | 32.07 | 49.09 |
| | XE | 4.5 | 5.6 | 5.7 | 4.8 | 45.49 | 5.01 | 6.38 | 7.05 | 13.17 | 15.37 |
| | DtoA | 2.0 | 2.1 | 2.0 | 1.3 | 41.76 | 2.14 | 2.31 | 4.21 | 6.06 | 8.53 |
| | DtoP | 5.6 | 2.1 | 1.6 | 1.2 | 16.19 | 8.97 | 9.37 | 15.47 | 24.68 | 20.95 |
| | N4nc | 100.0 | 100.0 | 100.0 | 100.0 | 100.00 | 100.00 | 100.00 | 100.00 | 100.00 | 100.00 |
| Product Composition | PIP | 5.87 | 8.00 | 8.44 | 8.20 | 3.58 | 4.06 | 4.02 | 3.75 | 2.71 | 2.91 |
| | DETA | 32.89 | 16.85 | 13.90 | 9.54 | 57.92 | 36.45 | 37.62 | 57.96 | 66.80 | 61.01 |
| (reactant and | AEEA | 16.69 | 8.17 | 7.08 | 7.18 | 1.39 | 17.03 | 16.29 | 13.77 | 11.02 | 7.15 |
| water-free basis) | AEP | 0.00 | 1.03 | .78 | 0.00 | 3.01 | 0.73 | 0.73 | 0.82 | 1.33 | 2.04 |
| | N4 | 2.21 | 1.98 | 2.15 | 2.90 | 13.69 | 1.59 | 2.24 | 3.98 | 7.45 | 11.14 |
| | N5 | 0.00 | 0.00 | 0.00 | 0.00 | 0.00 | 0.00 | 0.00 | 0.00 | 0.00 | 0.00 |
| | other | 40.07 | 61.27 | 64.82 | 68.17 | 20.10 | 39.03 | 38.03 | 18.16 | 9.54 | 14.91 |
| Leaching | P, ppm | 1.9 | <1 | <1 | — | — | 7.8 | — | 4.5 | 1.87 | <1 |

| | | Example | | | | | | | | | |
|---|---|---|---|---|---|---|---|---|---|---|---|
| | | 21 | 22 | 23 | 24 | 25 | 26 | 27 | 28 | 29 | 30 |
| Catalyst | ID | D | D | D | D | D | D | D | E | E | E |
| Operating Conditions | T | 290 | 290 | 300 | 290 | 290 | 300 | 290 | 310 | 310 | 300 |
| | P | 614.7 | 614.7 | 614.7 | 614.7 | 614.7 | 614.7 | 614.7 | 644.7 | 644.7 | 644.7 |
| | too | 309 | 412.2 | 514 | 610.6 | 706.7 | 802.7 | 1011.7 | 203.1 | 250 | 274.3 |
| | SVM | 13.11 | 11.01 | 9.46 | 16.20 | 13.12 | 12.39 | 10.66 | 6.04 | 14.95 | 17.37 |
| | EtoM | 1.99 | 1.99 | 1.99 | 1.99 | 1.99 | 1.99 | 1.99 | 1.99 | 1.99 | 1.99 |
| Calculated Results | XM | 21.80 | 24.01 | 34.46 | 16.11 | 17.26 | 27.53 | 20.09 | 77.7 | 13.9 | 6.6 |
| | XE | 9.76 | 8.77 | 12.70 | 8.01 | 8.80 | 10.33 | 8.80 | 48.1 | 7.5 | 6.7 |
| | DtoA | 4.20 | 4.56 | 5.23 | 3.60 | 3.47 | 4.29 | 3.72 | 18.9 | 3.3 | 2.7 |
| | DtoP | 28.49 | 28.86 | 25.57 | 27.65 | 26.89 | 25.48 | 25.05 | 11.1 | 9.6 | 5.8 |
| | N4nc | 100.00 | 100.00 | 100.00 | 100.00 | 100.00 | 100.00 | 100.00 | 100.0 | 100.0 | 100.0 |
| Product Composition | PIP | 2.38 | 2.58 | 2.60 | 2.46 | 2.47 | 2.60 | 2.68 | 4.33 | 4.75 | 6.39 |
| | DETA | 67.73 | 69.38 | 66.60 | 67.66 | 66.33 | 66.25 | 67.01 | 48.32 | 45.82 | 36.84 |
| (reactant and | AEEA | 16.13 | 15.21 | 12.75 | 18.81 | 19.09 | 15.43 | 18.00 | 2.56 | 13.82 | 13.58 |
| water-free basis) | AEP | 1.02 | 1.21 | 1.50 | 1.14 | 1.14 | 1.32 | 1.16 | 3.34 | 0.96 | 0.83 |
| | N4 | 6.01 | 4.86 | 7.66 | 4.30 | 3.20 | 5.93 | 3.07 | 10.77 | 3.29 | 2.12 |
| | N5 | 0.00 | 0.00 | 0.00 | 0.00 | 0.00 | 0.00 | 0.00 | 0.00 | 0.00 | 0.00 |
| | other | 5.82 | 5.93 | 8.15 | 4.79 | 6.98 | 7.71 | 7.24 | 30.18 | 30.47 | 39.54 |
| Leaching | P, ppm | 1.05 | <1 | <1 | <1 | <1 | <1 | | 37 | | |

-continued

|  |  | 31 | 32 | 33 | 34 | 35 | 36 | 37 | 38 | 39 | 40 |
|---|---|---|---|---|---|---|---|---|---|---|---|
| Catalyst | ID | F | F | F | F | F | F | F | F | F | F |
| Operating Conditions | T | 300 | 300 | 310 | 290 | 290 | 300 | 290 | 290 | 300 | 290 |
|  | P | 634.7 | 634.7 | 634.7 | 634.7 | 634.7 | 634.7 | 634.7 | 634.7 | 634.7 | 634.7 |
|  | too | 24 | 118.6 | 213.2 | 309 | 412.2 | 514 | 610.6 | 706.7 | 802.7 | 1011.7 |
|  | SVM | 9.53 | 10.76 | 12.16 | 11.79 | 10.36 | 9.50 | 16.04 | 13.86 | 12.62 | 10.98 |
|  | EtoM | 1.99 | 1.99 | 1.99 | 1.99 | 1.99 | 1.99 | 1.99 | 1.99 | 1.99 | 1.99 |
| Calculated Results | XM | 12.1 | 25.4 | 39.5 | 58.5 | 29.8 | 36.9 | 22.2 | 22.6 | 30.1 | 28.8 |
|  | XE | 7.1 | 12.3 | 14.3 | 50.0 | 10.5 | 15.0 | 10.0 | 10.5 | 11.6 | 11.2 |
|  | DtoA | 5.7 | 5.0 | 7.6 | 4.0 | 4.2 | 5.7 | 3.6 | 3.5 | 4.6 | 3.8 |
|  | DtoP | 11.9 | 25.4 | 22.6 | 29.3 | 29.3 | 27.9 | 33.2 | 31.1 | 26.4 | 29.6 |
|  | N4nc | 100.0 | 100.0 | 100.0 | 100.0 | 100.0 | 100.0 | 100.0 | 100.0 | 100.0 | 100.0 |
| Product Composition | PIP | 3.77 | 2.47 | 2.66 | 0.41 | 2.36 | 2.43 | 2.07 | 2.17 | 2.54 | 2.32 |
|  | DETA | 44.80 | 62.78 | 60.11 | 11.94 | 69.09 | 67.64 | 68.71 | 67.64 | 67.17 | 68.58 |
| (reactant and | AEEA | 7.79 | 12.62 | 7.95 | 3.00 | 16.60 | 11.91 | 19.01 | 19.51 | 14.46 | 18.24 |
| water-free basis) | AEP | 1.14 | 0.91 | 1.61 | 0.14 | 0.92 | 1.24 | 0.82 | 0.85 | 1.15 | 0.88 |
|  | N4 | 4.25 | 5.49 | 10.21 | 0.98 | 4.58 | 7.53 | 4.20 | 3.34 | 6.15 | 3.56 |
|  | N5 | 0.00 | 0.00 | 0.00 | 0.00 | 0.00 | 0.00 | 0.00 | 0.00 | 0.00 | 0.00 |
|  | other | 36.43 | 14.62 | 16.31 | 83.39 | 5.75 | 8.46 | 4.59 | 5.87 | 7.73 | 5.79 |
| Leaching | P, ppm | <1 | 2.77 | <1 | 2.47 | 1.66 | <1 | 1.97 | 1.6 | <1 |  |

|  |  | Example |  |  |  |  |  |  |  |  |  |
|---|---|---|---|---|---|---|---|---|---|---|---|
|  |  | 41 | 42 | 43 | 44 | 45 | 46 | 47 | 48 | 49 | 50 |
| Catalyst | ID | G | G | G | G | G | G | G | G | G | G |
| Operating Conditions | T | 300 | 310 | 310 | 290 | 300 | 290 | 310 | 310 | 290 | 300 |
|  | P | 614.7 | 614.7 | 614.7 | 614.7 | 614.7 | 614.7 | 614.7 | 614.7 | 614.7 | 614.7 |
|  | too | 23 | 119 | 215 | 311.5 | 407.6 | 517 | 610 | 705.5 | 801 | 993.5 |
|  | SVM | 13.99 | 11.89 | 9.06 | 11.47 | 6.93 | 8.69 | 6.28 | 8.56 | 10.21 | 9.19 |
|  | EtoM | 1.99 | 1.99 | 1.99 | 1.99 | 1.99 | 1.99 | 1.99 | 1.99 | 1.99 | 1.99 |
| Calculated Results | XM | 10.90 | 36.14 | 46.32 | 52.50 | 41.20 | 27.52 | 51.37 | 40.00 | 25.78 | 24.50 |
|  | XE | 6.00 | 12.28 | 11.98 | 5.91 | 14.42 | 10.48 | 16.96 | 15.04 | 8.52 | 9.54 |
|  | DtoA | 5.89 | 8.37 | 9.91 | 9.32 | 6.77 | 6.14 | 13.62 | 7.26 | 3.91 | 4.34 |
|  | DtoP | 30.25 | 27.25 | 18.18 | 60.43 | 30.52 | 28.68 | 20.75 | 24.89 | 32.66 | 27.00 |
|  | N4nc | 100.00 | 100.00 | 100.00 | 100.00 | 100.00 | 100.00 | 100.00 | 100.00 | 100.00 | 100.00 |
| Product Composition | PIP | 2.45 | 2.56 | 3.29 | 1.37 | 2.31 | 2.55 | 3.19 | 2.70 | 2.21 | 2.61 |
|  | DETA | 74.15 | 69.68 | 59.80 | 82.65 | 70.47 | 73.19 | 66.11 | 67.23 | 72.13 | 70.44 |
| (reactant and | AEEA | 12.59 | 8.33 | 6.03 | 8.87 | 10.41 | 11.93 | 4.85 | 9.26 | 18.46 | 16.22 |
| water-free basis) | AEP | 1.38 | 1.62 | 2.51 | 0.64 | 1.29 | 1.07 | 2.24 | 1.78 | 0.89 | 1.11 |
|  | N4 | 1.43 | 9.17 | 15.26 | 3.47 | 7.94 | 1.25 | 10.12 | 9.51 | 0.39 | 3.93 |
|  | N5 | 0.00 | 0.00 | 0.00 | 0.00 | 0.00 | 0.00 | 0.00 | 0.00 | 0.00 | 0.00 |
|  | other | 6.92 | 8.01 | 12.44 | 2.62 | 7.06 | 9.68 | 13.37 | 9.13 | 5.68 | 5.37 |
| Leaching | P, ppm |  |  |  |  |  |  |  |  |  |  |

|  |  | Example |  |  |  |  |  |  |  |  |  |
|---|---|---|---|---|---|---|---|---|---|---|---|
|  |  | 51 | 52 | 53 | 54 | 55 | 56 | 57 | 58 | 59 | 60 |
| Catalyst | ID | H | H | H | I | I | I | I | I | I | I |
| Operating Conditions | T | 310 | 300 | 300 | 300 | 310 | 310 | 290 | 300 | 290 | 310 |
|  | P | 614.7 | 614.7 | 614.7 | 644.7 | 644.7 | 644.7 | 644.7 | 644.7 | 644.7 | 644.7 |
|  | too | 49 | 73 | 144.3 | 23 | 119 | 215 | 311.5 | 407.6 | 517 | 610 |
|  | SVM | 11.28 | 8.35 | 7.75 | 15.16 | 13.89 | 12.70 | 18.05 | 10.11 | 14.48 | 11.51 |
|  | EtoM | 1.99 | 1.99 | 1.99 | 1.99 | 1.99 | 1.99 | 1.99 | 1.99 | 1.99 | 1.99 |
| Calculated Results | XM | 1.04 | 0.48 | 0.46 | 15.9 | 27.0 | 30.4 | 41.0 | 26.6 | 14.4 | 26.8 |
|  | XE | 5.98 | 5.24 | 5.79 | 8.0 | 8.9 | 9.8 | 10.7 | 9.5 | 5.5 | 11.7 |
|  | DtoA | 1.29 | 1.68 | 1.57 | 4.7 | 6.2 | 5.9 | 10.8 | 4.7 | 4.1 | 5.7 |
|  | DtoP | 1.32 | 1.18 | 1.34 | 18.4 | 21.0 | 20.7 |  | 23.0 | 23.7 | 20.3 |
|  | N4nc | 100.00 | 100.00 | 100.00 | 100.0 | 100.0 | 100.0 | 100.00 | 100.0 | 100.0 | 100.0 |
| Product Composition | PIP | 8.55 | 10.28 | 10.06 | 3.54 | 3.13 | 3.07 | 0.00 | 2.83 | 2.91 | 3.12 |
|  | DETA | 11.68 | 12.11 | 13.43 | 65.27 | 65.84 | 63.40 | 87.51 | 65.19 | 68.87 | 63.28 |
| (reactant and | AEEA | 9.07 | 7.21 | 8.58 | 13.78 | 10.61 | 10.78 | 8.13 | 13.96 | 16.68 | 11.12 |
| water-free basis) | AEP | 1.15 | 1.36 | 1.25 | 1.39 | 1.58 | 1.67 | 0.66 | 1.28 | 1.13 | 1.62 |
|  | N4 | 2.68 | 3.50 | 1.17 | 1.84 | 5.79 | 7.29 | 2.33 | 5.67 | 2.75 | 5.57 |
|  | N5 | 0.00 | 0.00 | 0.00 | 0.00 | 0.00 | 0.00 | 0.00 | 0.00 | 0.00 | 0.00 |
|  | other | 63.29 | 61.19 | 61.45 | 12.87 | 11.80 | 12.59 | 0.83 | 10.01 | 8.84 | 15.10 |
| Leaching | P, ppm | <1 | <1 | <1 |  |  |  |  |  |  |  |

|  |  | Example |  |  |  |  |  |  |  |  |  |
|---|---|---|---|---|---|---|---|---|---|---|---|
|  |  | 61 | 62 | 63 | 64 | 65 | 66 | 67 | 68 | 69 | 70 |
| Catalyst | ID | I | I | I | J | J | J | J | J | J | J |
| Operating Conditions | T | 310 | 290 | 300 | 290 | 300 | 300 | 300 | 300 | 300 | 300 |
|  | P | 644.7 | 644.7 | 644.7 | 614.7 | 614.7 | 614.7 | 614.7 | 639.7 | 639.7 | 639.7 |
|  | too | 705.5 | 801 | 993.5 | 48.5 | 149.5 | 264 | 362.5 | 457.5 | 505 | 600 |
|  | SVM | 12.42 | 17.43 | 16.84 | 18.84 | 18.49 | 15.11 | 14.84 | 15.69 | 14.78 | 11.92 |
|  | EtoM | 1.99 | 1.99 | 1.99 | 2.03 | 2.03 | 2.03 | 2.03 | 2.03 | 2.03 | 2.03 |
| Calculated Results | XM | 21.4 | 9.9 | 11.2 | 5.47 | 12.47 | 16.49 | 19.05 | 16.42 | 19.27 | 19.17 |
|  | XE | 9.9 | 6.2 | 4.4 | 2.33 | 3.58 | 4.31 | 4.74 | 5.34 | 5.85 | 5.10 |
|  | DtoA | 4.8 | 3.3 | 4.1 | 4.79 | 4.60 | 5.05 | 4.32 | 4.78 | 4.68 |  |
|  | DtoP | 21.0 | 30.0 | 23.3 | 45.90 | 41.55 | 39.46 | 38.77 | 38.45 | 35.26 | 35.21 |
|  | N4nc | 100.0 | 100.0 | 100.0 | 71.23 | 32.64 | 65.62 | 77.90 | 68.86 | 70.21 | 69.17 |
| Product Composition | PIP | 3.12 | 2.24 | 2.91 | 1.42 | 1.65 | 1.75 | 1.78 | 1.72 | 1.88 | 1.88 |
|  | DETA | 65.45 | 67.14 | 67.94 | 65.04 | 68.38 | 69.20 | 69.09 | 66.26 | 66.31 | 66.37 |
| (reactant and | AEEA | 13.70 | 20.09 | 16.48 | 13.56 | 15.15 | 15.06 | 13.69 | 15.34 | 13.86 | 14.18 |

-continued

|  |  |  |  |  |  |  |  |  |  |  |
|---|---|---|---|---|---|---|---|---|---|---|
| water-free basis) | AEP | 1.51 | 0.98 | 1.22 | 0.79 | 0.64 | 0.66 | 0.70 | 0.76 | 0.74 | 0.72 |
|  | N4 | 4.62 | 0.56 | 0.00 | 2.52 | 1.89 | 3.38 | 3.52 | 3.96 | 4.00 | 3.80 |
|  | N5 | 0.00 | 0.00 | 0.00 | 0.00 | 0.00 | 0.51 | 0.50 | 0.76 | 0.63 | 0.57 |
|  | other | 10.73 | 8.23 | 10.70 | 16.19 | 11.92 | 9.09 | 10.22 | 10.57 | 11.99 | 12.05 |
| Leaching | P, ppm |  |  |  | 21.8 | 2.36 | 1.12 | <1 | <1 | <1 | 1.18 |

| | | Example | | | | | | | | |
|---|---|---|---|---|---|---|---|---|---|---|
| | | 71 | 72 | 73 | 74 | 75 | 76 | 77 | 78 | 79 | 80 |
| Catalyst | ID | J | J | J | J | K | K | K | K | K | K |
| Operating Conditions | T | 300 | 290 | 300 | 300 | 290 | 300 | 300 | 300 | 300 | 300 |
|  | P | 639.7 | 639.7 | 639.7 | 639.7 | 614.7 | 614.7 | 614.7 | 614.7 | 614.7 | 614.7 |
|  | too | 696 | 701.5 | 910.5 | 981.5 | 75.5 | 175.5 | 290 | 387.5 | 483.5 | 531 |
|  | SVM | 13.15 | 12.19 | 11.06 | 11.77 | 19.47 | 18.30 | 16.47 | 15.65 | 16.98 | 16.59 |
|  | EtoM | 2.03 | 2.03 | 2.03 | 2.03 | 2.03 | 2.03 | 2.03 | 2.03 | 2.03 | 2.03 |
| Calculated Results | XM | 21.70 | 14.59 | 21.97 | 23.29 | 6.8 | 22.0 | 25.2 | 26.0 | 22.0 | 23.7 |
|  | XE | 6.49 | 5.32 | 6.13 | 6.15 | 2.6 | 6.8 | 7.4 | 7.5 | 7.2 | 7.7 |
|  | DtoA | 5.03 | 3.92 | 4.68 | 4.61 | 4.1 | 4.5 | 6.7 | 6.4 | 4.7 | 5.2 |
|  | DtoP | 27.36 | 45.44 | 28.49 | 26.83 | 36.3 | 33.7 | 30.7 | 32.0 | 32.5 | 31.2 |
|  | N4nc | 74.65 | 71.67 | 76.79 | 75.65 | 74.7 | 84.0 | 84.8 | 86.6 | 86.6 | 85.3 |
| Product Composition | PIP | 2.43 | 1.49 | 2.38 | 2.48 | 1.80 | 2.10 | 2.36 | 2.26 | 2.15 | 2.25 |
|  | DETA | 66.59 | 67.85 | 67.70 | 66.42 | 65.29 | 70.65 | 72.51 | 72.24 | 69.68 | 70.20 |
| (reactant and | AEEA | 13.24 | 17.33 | 14.46 | 14.41 | 15.88 | 15.65 | 10.85 | 11.23 | 14.79 | 13.52 |
| water-free basis) | AEP | 0.83 | 0.64 | 0.84 | 0.87 | 0.57 | 0.57 | 0.79 | 0.76 | 0.67 | 0.71 |
|  | N4 | 4.54 | 2.81 | 3.24 | 4.64 | 3.18 | 4.13 | 5.84 | 5.48 | 5.45 | 5.51 |
|  | N5 | 0.66 | 0.68 | 0.19 | 0.66 | 0.00 | 0.31 | 0.44 | 0.42 | 0.28 | 0.51 |
|  | other | 11.27 | 8.81 | 10.84 | 10.15 | 12.90 | 6.48 | 7.07 | 7.42 | 6.80 | 7.12 |
| Leaching | P, ppm | <1 | <1 | <1 | <1 | <1 | <1 | <1 | <1 | <1 | 1.07 |

| | | Example | | | | | | | | |
|---|---|---|---|---|---|---|---|---|---|---|
| | | 81 | 82 | 83 | 84 | 85 | 86 | 87 | 88 | 89 | 90 |
| Catalyst | ID | K | K | K | K | K | L | L | L | L | L |
| Operating Conditions | T | 300 | 300 | 290 | 300 | 300 | 300 | 290 | 310 | 310 | 299.3 |
|  | P | 614.7 | 614.7 | 614.7 | 614.7 | 614.7 | 614.7 | 614.7 | 614.7 | 614.7 | 614.7 |
|  | too | 627 | 723 | 728.5 | 938.5 | 1010.5 | 24.5 | 102 | 197.5 | 311.5 | 411.5 |
|  | SVM | 16.29 | 13.92 | 12.68 | 11.78 | 11.79 | 17.27 | 16.51 | 15.89 | 13.37 | 11.05 |
|  | EtoM | 2.03 | 2.03 | 2.03 | 2.03 | 2.03 | 2.03 | 2.03 | 2.03 | 2.03 | 2.03 |
| Calculated Results | XM | 22.5 | 25.0 | 17.0 | 23.7 | 22.9 | 3.11 | 7.16 | 30.45 | 47.40 | 36.73 |
|  | XE | 6.8 | 7.8 | 6.0 | 6.7 | 7.1 | 4.69 | 6.07 | 12.50 | 19.91 | 13.02 |
|  | DtoA | 4.8 | 4.6 | 4.2 | 4.7 | 4.5 | 79.59 | 7.58 | 12.64 | 12.78 | 9.57 |
|  | DtoP | 30.5 | 29.0 | 43.5 | 24.1 | 22.8 | 9.87 | 26.33 | 23.11 | 20.60 | 25.26 |
|  | N4nc | 82.9 | 82.3 | 78.1 | 79.6 | 78.8 | 81.13 | 79.43 | 75.16 | 87.52 | 58.52 |
| Product Composition | PIP | 2.29 | 2.36 | 1.60 | 2.75 | 2.87 | 4.86 | 2.38 | 2.99 | 2.74 | 2.72 |
|  | DETA | 69.75 | 68.28 | 69.64 | 66.35 | 65.52 | 47.97 | 62.48 | 69.19 | 56.36 | 68.78 |
| (reactant and | AEEA | 14.43 | 14.88 | 16.71 | 14.23 | 14.52 | 0.60 | 8.24 | 5.47 | 4.41 | 7.19 |
| water-free basis) | AEP | 0.68 | 0.73 | 0.60 | 1.28 | 0.82 | 1.31 | 1.27 | 0.29 | 2.09 | 1.25 |
|  | N4 | 4.54 | 4.75 | 3.24 | 3.47 | 3.73 | 11.53 | 6.81 | 5.89 | 17.67 | 3.64 |
|  | N5 | 0.52 | 0.60 | 0.35 | 0.42 | 0.11 | 5.63 | 0.96 | 0.52 | 3.52 | 0.18 |
|  | other | 7.62 | 8.20 | 7.67 | 11.21 | 12.16 | 28.09 | 17.85 | 15.65 | 13.21 | 16.24 |
| Leaching | P, ppm | <1 | <1 | <1 | <1 | <1 | <1 | 1.08 |  | <1 | <1 |

| | | Example | | | | | | | | |
|---|---|---|---|---|---|---|---|---|---|---|
| | | 91 | 92 | 93 | 94 | 95 | 96 | 97 | 98 | 99 | 100 |
| Catalyst | ID | L | L | L | L | L | L | M | M | M | M |
| Operating Conditions | T | 300 | 310 | 300 | 310 | 300 | 300 | 300 | 290 | 310 | 310 |
|  | P | 614.7 | 614.7 | 614.7 | 614.7 | 614.7 | 614.7 | 614.7 | 639.7 | 639.7 | 639.7 |
|  | too | 512.5 | 609 | 706.5 | 802 | 904 | 1018 | 24.5 | 102 | 197.5 | 311.5 |
|  | SVM | 13.42 | 9.41 | 11.00 | 14.04 | 12.34 | 9.95 | 19.41 | 17.91 | 17.45 | 13.78 |
|  | EtoM | 2.03 | 2.03 | 2.03 | 2.03 | 2.03 | 2.03 | 2.03 | 2.03 | 2.03 | 2.03 |
| Calculated Results | XM | 29.98 | 53.99 | 35.14 | 76.82 | 34.78 | 36.36 | 11.36 | 10.42 | 31.48 | 45.64 |
|  | XE | 11.66 | 14.91 | 8.22 | 60.65 | 11.79 | 15.72 | 2.83 | 6.18 | 11.96 | 16.75 |
|  | DtoA | 8.93 | 21.87 | 10.63 | 15.98 | 5.16 | 5.13 | 7.26 | 5.07 | 10.46 | 12.66 |
|  | DtoP | 26.73 | 15.49 | 27.00 | 15.77 | 34.70 | 34.18 | 23.94 | 41.10 | 27.78 | 27.70 |
|  | N4nc | 64.18 | 83.71 | 54.15 | 27.08 | 100.00 | 100.00 | 100.00 | 81.62 | 81.57 | 89.86 |
| Product Composition | PIP | 2.71 | 3.63 | 2.78 | 0.49 | 1.94 | 1.88 | 2.74 | 1.62 | 2.61 | 2.32 |
|  | DETA | 72.49 | 56.19 | 75.15 | 7.68 | 67.43 | 64.40 | 65.55 | 66.69 | 72.62 | 64.33 |
| (reactant and | AEEA | 8.12 | 2.57 | 7.07 | 0.48 | 13.08 | 12.55 | 9.02 | 13.15 | 6.94 | 5.08 |
| water-free basis) | AEP | 1.22 | 0.04 | 1.32 | 0.26 | 0.96 | 1.00 | 1.46 | 1.38 | 0.29 | 1.73 |
|  | N4 | 3.37 | 17.14 | 3.10 | 0.35 | 6.38 | 7.47 | 7.57 | 6.04 | 6.37 | 16.10 |
|  | N5 | 0.00 | 2.46 | 0.00 | 0.00 | 0.00 | 0.00 | 0.00 | 0.00 | 0.09 | 1.31 |
|  | other | 12.09 | 17.98 | 10.58 | 90.75 | 10.22 | 12.69 | 13.66 | 11.12 | 11.06 | 9.12 |
| Leaching | P, ppm | <1 | <1 | <1 | <1 | <1 | <1 | <1 | <1 | <1 | <1 |

| | | Example | | | | | | | | |
|---|---|---|---|---|---|---|---|---|---|---|
| | | 101 | 102 | 103 | 104 | 105 | 106 | 107 | 108 | 109 | 110 |
| Catalyst | ID | M | M | M | M | M | M | M | N | N | N |
| Operating Conditions | T | 299.3 | 300 | 310 | 300 | 310 | 300 | 300 | 300 | 300 | 310 |
|  | P | 639.7 | 639.7 | 639.7 | 639.7 | 639.7 | 639.7 | 639.7 | 614.7 | 614.7 | 614.7 |
|  | too | 411.5 | 512.5 | 609 | 706.5 | 802 | 904 | 1018 | 25 | 30.5 | 104 |
|  | SVM | 10.31 | 13.23 | 9.66 | 10.82 | 12.09 | 13.08 | 9.39 | 13.49 | 14.53 | 10.68 |
|  | EtoM | 2.03 | 2.03 | 2.03 | 2.03 | 2.03 | 2.03 | 2.03 | 2.03 | 2.03 | 2.03 |
| Calculated Results | XM | 32.94 | 24.59 | 47.43 | 30.01 | 40.17 | 28.79 | 31.03 | 27.56 | 27.53 | 56.81 |

-continued

|  |  |  |  |  |  |  |  |  |  |  |
|---|---|---|---|---|---|---|---|---|---|---|
|  | XE | 13.68 | 11.70 | 18.50 | 5.93 | 4.67 | 8.86 | 12.63 | 9.77 | 8.54 | 19.12 |
|  | DtoA | 10.14 | 13.17 | 19.60 | 21.87 | 25.15 | 4.64 | 4.60 | 11.04 | 8.85 | 12.26 |
|  | DtoP | 40.81 | 35.33 | 17.62 | 19.59 | 14.76 | 26.88 | 23.93 | 40.70 | 42.47 | 30.69 |
|  | N4nc | 67.64 | 54.97 | 79.65 | 43.31 | 42.45 | 100.00 | 100.00 | 100.00 | 100.00 | 100.00 |
| Product Composition | PIP | 1.81 | 2.11 | 3.29 | 3.68 | 4.39 | 2.37 | 2.47 | 1.66 | 1.62 | 2.12 |
|  | DETA | 73.72 | 74.65 | 57.88 | 72.03 | 64.81 | 63.58 | 59.00 | 67.70 | 69.01 | 64.95 |
| (reactant and | AEEA | 7.27 | 5.67 | 2.95 | 3.29 | 2.58 | 13.71 | 12.83 | 6.13 | 7.80 | 5.30 |
| water-free basis) | AEP | 0.99 | 1.09 | 2.25 | 1.32 | 2.31 | 1.07 | 1.25 | 1.25 | 1.19 | 1.68 |
|  | N4 | 2.64 | 2.72 | 13.87 | 2.75 | 2.63 | 5.10 | 6.10 | 5.80 | 5.73 | 12.20 |
|  | N5 | 0.29 | 0.00 | 1.23 | 0.00 | 0.60 | 0.00 | 0.00 | 0.00 | 0.00 | 0.00 |
|  | other | 13.28 | 13.75 | 18.53 | 16.92 | 22.67 | 14.18 | 18.36 | 17.45 | 14.65 | 13.75 |
| Leaching | P, ppm | <1 | <1 | <1 | <1 | <1 | <1 | <1 | <1 | <1 | <1 |

|  |  | Example |  |  |  |  |  |  |  |  |  |
|---|---|---|---|---|---|---|---|---|---|---|---|
|  |  | 111 | 112 | 113 | 114 | 115 | 116 | 117 | 118 | 119 | 120 |
| Catalyst | ID | N | N | N | N | O | O | O | O | O | O |
| Operating Conditions | T | 290 | 310 | 300 | 310 | 300 | 300 | 310 | 290 | 310 | 300 |
|  | P | 624.7 | 624.7 | 624.7 | 624.7 | 614.7 | 614.7 | 614.7 | 644.7 | 644.7 | 644.7 |
|  | too | 200 | 301 | 398.5 | 441.5 | 25 | 30.5 | 104 | 200 | 301 | 398.5 |
|  | SVM | 10.17 | 10.18 | 13.30 | 11.90 | 15.80 | 17.14 | 13.67 | 10.40 | 11.84 | 14.65 |
|  | EtoM | 2.03 | 2.03 | 2.03 | 2.03 | 2.03 | 2.03 | 2.03 | 2.03 | 2.03 | 2.03 |
| Calculated Results | XM | 38.36 | 51.70 | 35.43 | 50.08 | 17.5 | 18.7 | 43.0 | 36.9 | 44.1 | 27.7 |
|  | XE | 11.24 | 15.03 | 12.08 | 15.23 | 4.9 | 4.8 | 13.0 | 10.9 | 13.6 | 9.4 |
|  | DtoA | 4.77 | 7.61 | 5.17 | 7.41 | 3.5 | 3.7 | 7.9 | 4.7 | 7.4 | 5.1 |
|  | DtoP | 42.52 | 26.45 | 39.59 | 28.22 | 37.3 | 41.8 | 33.2 | 44.9 | 30.7 | 38.0 |
|  | N4nc | 100.00 | 100.00 | 100.00 | 100.00 | 100.00 | 100.00 | 100.00 | 100.00 | 100.00 | 100.00 |
| Product Composition | PIP | 1.64 | 2.49 | 1.77 | 2.33 | 1.73 | 1.57 | 2.01 | 1.57 | 2.21 | 1.85 |
|  | DETA | 69.88 | 65.76 | 70.20 | 65.65 | 64.43 | 65.70 | 66.80 | 70.30 | 67.89 | 70.21 |
| (reactant and | AEEA | 14.64 | 8.64 | 13.59 | 8.86 | 18.24 | 17.86 | 8.50 | 14.90 | 9.16 | 13.69 |
| water-free basis) | AEP | 0.76 | 1.61 | 0.82 | 1.40 |  |  |  |  | 1.42 | 0.99 |
|  | N4 | 6.90 | 12.22 | 6.30 | 11.33 | 3.37 | 3.76 | 10.72 | 6.83 | 11.40 | 5.55 |
|  | N5 | 0.00 | 0.00 | 0.00 | 0.00 | 0.00 | 0.00 | 0.00 | 0.00 | 0.00 | 0.00 |
|  | other | 6.17 | 8.83 | 6.72 | 9.79 | 11.53 | 10.46 | 10.57 | 5.71 | 7.14 | 6.98 |
| Leaching | P, ppm |  | 1.91 | <1 | <1 | <1 | <1 | <1 |  | <1 | <1 |

|  |  | Example |  |  |  |  |  |  |  |  |  |
|---|---|---|---|---|---|---|---|---|---|---|---|
|  |  | 121 | 122 | 123 | 124 | 125 | 126 | 127 | 128 | 129 | 130 |
| Catalyst | ID | O | P | P | P | P | P | Q | Q | Q | Q |
| Operating Conditions | T | 310 | 300 | 300 | 310 | 300 | 300 | 300 | 300 | 310 | 300 |
|  | P | 644.7 | 614.7 | 614.7 | 614.7 | 614.7 | 614.7 | 614.7 | 614.7 | 614.7 | 614.7 |
|  | too | 441.5 | 24 | 61.5 | 148.8 | 215.8 | 278 | 24 | 61.5 | 148.8 | 215.8 |
|  | SVM | 13.24 | 11.69 | 17.73 | 16.78 | 15.35 | 18.20 | 9.91 | 11.54 | 12.54 | 11.81 |
|  | EtoM | 2.03 | 1.99 | 1.99 | 1.99 | 1.99 | 1.99 | 1.99 | 1.99 | 1.99 | 1.99 |
| Calculated Results | M | 38.3 | 21.61 | 33.52 | 42.94 | 33.32 | 33.04 | 3.3 | 18.5 | 25.6 | 20.7 |
|  | E | 13.7 | 11.08 | 14.25 | 15.76 | 14.77 | 15.33 | 5.3 | 8.3 | 10.6 | 9.8 |
|  | DtoA | 6.5 | 10.60 | 6.93 | 8.51 | 5.33 | 4.73 | 8.0 | 5.8 | 5.6 | 4.3 |
|  | DtoP | 32.2 | 25.72 | 33.87 | 22.83 | 32.81 | 33.76 | 12.1 | 17.5 | 19.1 | 22.3 |
|  | N4nc | 100.0 | 100.00 | 100.00 | 100.00 | 100.00 | 100.00 | 100.0 | 100.0 | 100.0 | 100.0 |
| Product Composition | PIP | 2.06 | 2.99 | 2.16 | 2.87 | 2.16 | 2.08 | 5.54 | 3.90 | 3.45 | 3.08 |
|  | DETA | 66.32 | 77.04 | 73.05 | 65.47 | 70.85 | 70.05 | 66.98 | 68.35 | 65.75 | 68.92 |
| (reactant and | AEEA | 10.26 | 7.27 | 10.55 | 7.69 | 13.28 | 14.82 | 8.39 | 11.89 | 11.82 | 16.11 |
| water-free basis) | AEP | 1.30 | 0.77 | 1.05 | 1.90 | 1.08 | 1.00 | 0.88 | 1.59 | 1.75 | 1.24 |
|  | N4 | 10.52 | 2.83 | 6.43 | 11.29 | 7.10 | 6.51 | 2.83 | 4.11 | 6.85 | 4.26 |
|  | N5 | 0.00 | 0.00 | 0.00 | 0.00 | 0.00 | 0.00 | 0.00 | 0.00 | 0.00 | 0.00 |
|  | other | 8.80 | 9.11 | 6.60 | 10.54 | 5.34 | 5.34 | 15.38 | 9.89 | 9.98 | 6.06 |
| Leaching | P, ppm | <1 |  |  |  |  |  |  |  |  |  |

|  |  |  | Example |  |  |  |  |  |
|---|---|---|---|---|---|---|---|---|
|  |  |  | 131 | 132 | 133 | 134 | 135 | 136 |
| Catalyst | ID | Q | R | R | R | R | R |
| Operating Conditions | T | 300 | 300 | 300 | 310 | 310 | 300 |
|  | P | 614.7 | 614.7 | 614.7 | 614.7 | 614.7 | 614.7 |
|  | too | 278 | 25.7 | 70.8 | 150.75 | 285 | 308 |
|  | SVM | 14.86 | 13.27 | 14.28 | 19.20 | 14.44 | 16.82 |
|  | EtoM | 1.99 | 1.99 | 1.99 | 1.99 | 1.99 | 1.99 |
| Calculated Results | M | 19.7 | 14.57 | 14.49 | 37.26 | 40.61 | 24.16 |
|  | E | 9.1 | 7.03 | 6.04 | 8.09 | 12.55 | 7.55 |
|  | DtoA | 4.1 | 2.94 | 3.55 | 16.41 | 14.17 | 24.74 |
|  | DtoP | 21.9 | 37.05 | 40.02 | 36.66 | 36.17 | 41.65 |
|  | N4nc | 100.0 | 100.00 | 100.00 | 100.00 | 100.00 |  |
| Product Composition | PIP | 3.10 | 1.73 | 1.77 | 2.26 | 2.17 | 2.18 |
|  | DETA | 67.94 | 64.05 | 71.01 | 82.87 | 78.64 | 90.75 |
| (reactant and | AEEA | 16.77 | 21.77 | 19.99 | 5.05 | 5.55 | 3.67 |
| water-free basis) | AEP | 1.19 | 2.26 | 0.58 | 0.99 | 1.12 | 0.75 |
|  | N4 | 3.72 | 1.06 | 0.50 | 3.53 | 6.00 | 0.00 |
|  | N5 | 0.00 | 0.00 | 0.00 | 0.00 | 0.00 | 0.00 |
|  | other | 7.02 | 8.28 | 6.14 | 5.31 | 6.51 | 2.66 |
| Leaching | P, ppm |  |  |  |  |  |  |

Whereas the preceding examples utilized EDA and MEA as feedstocks, the following examples utilize

|  |  | Example | | | |
|---|---|---|---|---|---|
|  |  | 137 | 138 | 139 | 140 |
| Catalyst | ID | G | G | G | G |
| Operating Conditions | T | 300 | 300 | 300 | 300 |
|  | P | 600 | 600 | 600 | 600 |
|  | too | 1104 | 1109 | 1128 | 1133 |
|  | SVM | 7.1 | 10.2 | 10.9 | 12.8 |
|  | DETA/MEA | 1 | 1 | 1 | 1 |
| Calculated Results | XM | 46.5 | 33 | 38.7 | 24.5 |
| Product Composition | EDA | 0.42 | 3.69 | 0 | 4.41 |
| (reactant and | PIP | 2.25 | 2.71 | 2.02 | 2.64 |
| water-free) | AEEA | 9.95 | 8.44 | 11.86 | 9.95 |
|  | AEP | 5.09 | 5.17 | 4.49 | 4.92 |
|  | TAEA | 11.75 | 11.22 | 12.74 | 11.66 |
|  | L-TETA | 54.52 | 55.47 | 55.52 | 53.72 |
|  | others | 16.85 | 13.39 | 13.36 | 12.69 |

|  |  | Example | | | |
|---|---|---|---|---|---|
|  |  | 141 | 142 | 143 | 144 |
| Catalyst | ID | G | G | G | G |
| Operating Conditions | T | 300 | 300 | 300 | 300 |
|  | P | 600 | 600 | 600 | 600 |
|  | too | 1199 | 1203 | 1240 | 1244 |
|  | SV(AEEA) | 6.1 | 6.9 | 6.5 | 6.1 |
|  | EDA/AEEA | 2 | 2 | 2 | 2 |
| Calculated Results | XAEEA | 29 | 23.3 | 24.6 | 18 |
| Product Composition | MEA | 1.62 | 1.77 | 1.7 | 1.85 |
| (reactant and | PIP | 22.5 | 22.7 | 22.54 | 23.3 |
| water-free) | DETA | 4.31 | 4.99 | 4.34 | 3.6 |
|  | AEP | 0.9 | 0.9 | 0.8 | 0.7 |
|  | HEP | 0.7 |  | 0.8 | 0.7 |
|  | L-TETA | 54.73 | 69.6 | 54.48 | 53.6 |
|  | others | 15.3 | 19.09 | 15.4 | 16.1 |

I claim:

1. A method for making a catalyst composition for the condensation of alcohols with amines to produce an enhanced ratio of acyclic polyamines to other reaction products, comprising reacting at a temperature of about 425° to about 625° C.: (a) high surface area titanium oxide or titanium oxide precursor, or mixtures thereof, Co) a phosphorus component, and (c) metal oxide or metal oxide precursor, of metals selected from the group consisting of Na, mixture of Li and Na, mixture of K and Na, mixture of Ba and Na, mixture of Na and Ca, mixture of Na and Mg and mixture of Na and La, for a period of time sufficient to produce at least one catalytically active phosphate species, wherein the mole ratios of component (a) calculated as $MO_2$ wherein M is Ti, Co) calculated as $P_2O_5$ and (c) calculated as metal oxide ($M'_xO_y$) wherein M' is Na, Li, K. Ba, Ca, Mg, or La, x is 1 or 2 and y is 1 or 3, in the catalyst formed fall within the compositional area defined by points I-J-K-L-I of FIG. 1.

2. The method of claim 1 wherein the metal for (c) is Na.

3. The method of claim 1 wherein (c) is present in an amount of 20 to 30 mole percent of the composition.

4. A catalyst composition produced by the method of claim 1.

5. A catalyst composition produced by the method of claim 3.

6. The catalyst composition of claim 4 wherein the catalyst composition has a pH greater than about 7.

7. The catalyst composition of claim 6 wherein the metal for (c) is Na.

* * * * *